United States Patent
Van Agthoven

(10) Patent No.: US 9,903,795 B2
(45) Date of Patent: Feb. 27, 2018

(54) COMPOSITION FOR HIGH STRINGENCY CELL TREATMENT AND ANTIGEN RETRIEVAL

(71) Applicant: Beckman Coulter, Inc., Brea, CA (US)

(72) Inventor: Andreas Van Agthoven, Marseilles (FR)

(73) Assignee: Beckman Coulter, Inc., Brea, CA (US)

( * ) Notice: Subject to any disclaimer, the term of this patent is extended or adjusted under 35 U.S.C. 154(b) by 372 days.

(21) Appl. No.: 14/139,158

(22) Filed: Dec. 23, 2013

(65) Prior Publication Data

US 2014/0186858 A1 Jul. 3, 2014

Related U.S. Application Data

(60) Provisional application No. 61/747,044, filed on Dec. 28, 2012.

(51) Int. Cl.
*G01N 1/10* (2006.01)
*G01N 1/30* (2006.01)

(52) U.S. Cl.
CPC .................... *G01N 1/30* (2013.01)

(58) Field of Classification Search
None
See application file for complete search history.

(56) References Cited

U.S. PATENT DOCUMENTS 6,969,591 B2 * 11/2005 Hara .................. G01N 33/6893
422/161
2006/0178294 A1 8/2006 Van Agthoven et al.

FOREIGN PATENT DOCUMENTS

WO WO 2004/007723 A2 1/2004

OTHER PUBLICATIONS

Goodwin et al., "An Introduction to Forensic Genetics," John Wiley & Sons, Ltd., 2007, p. 29.*
Promega "Buffers for Biochemical Reactions," retrieved from https://www.promega.com/~/media/files/resources/paguide/a4/chap15a4.pdf?la=en on Mar. 21, 2016.*
A printout retrieved from http://www.sigmaaldrich.com/catalog/product/sigma/p5556?lang=en&region=US on Oct. 5, 2017.*
Byun, N. et al., "Axonal and periaxonal swelling precede peripheral neurodegeneration in KCC3 knockout mice," *Neurobiology of Disease*, vol. 28, pp. 39-51 (2007).
International Search Report and Written Opinion for PCT/US2013/077518 dated Apr. 4, 2014.
Sambrook, J. et al., "Stock solutions," *Molecular Cloning: A Laboratory Manual*, vol. 3, 2nd edition, Cold Spring Harbor Laboratory Press, 1 page (1989).
Triethanolamine Lauryl Sulfate Cas#: 139-96-8, retrieved from http://www.chemicalbook.com/ProductChemicalPropertiesCB3193301_EN.htm, 1 page (Copyright 2008).
van de Wetering, D. et al., "IFN-α cannot substitute lack of IFN-γ responsiveness in cells of an IFN-γR1 deficient patient," *Clinical Immunology*, vol. 138, pp. 282-290 (2011).
Santos et al., "A systematic study of bovine serum albumin (BSA) and sodium dodecyl sulfate (SDS) interactions by surface tension and small angle X-ray scattering," Journal of Colloid and Interface Science, (2003) pp. 400-408.

* cited by examiner

*Primary Examiner* — Galina Yakovleva
(74) *Attorney, Agent, or Firm* — Merchant & Gould P.C.

(57) ABSTRACT

The present invention relates to a cell treatment composition for the permeabilization of fixed blood cells, to the use of said composition, to a method for the treatment of a biological sample comprising fixation of said sample and subsequently contacting said biological sample with said cell treatment composition. The invention further relates and to a kit comprising said cell treatment composition.

22 Claims, 1 Drawing Sheet

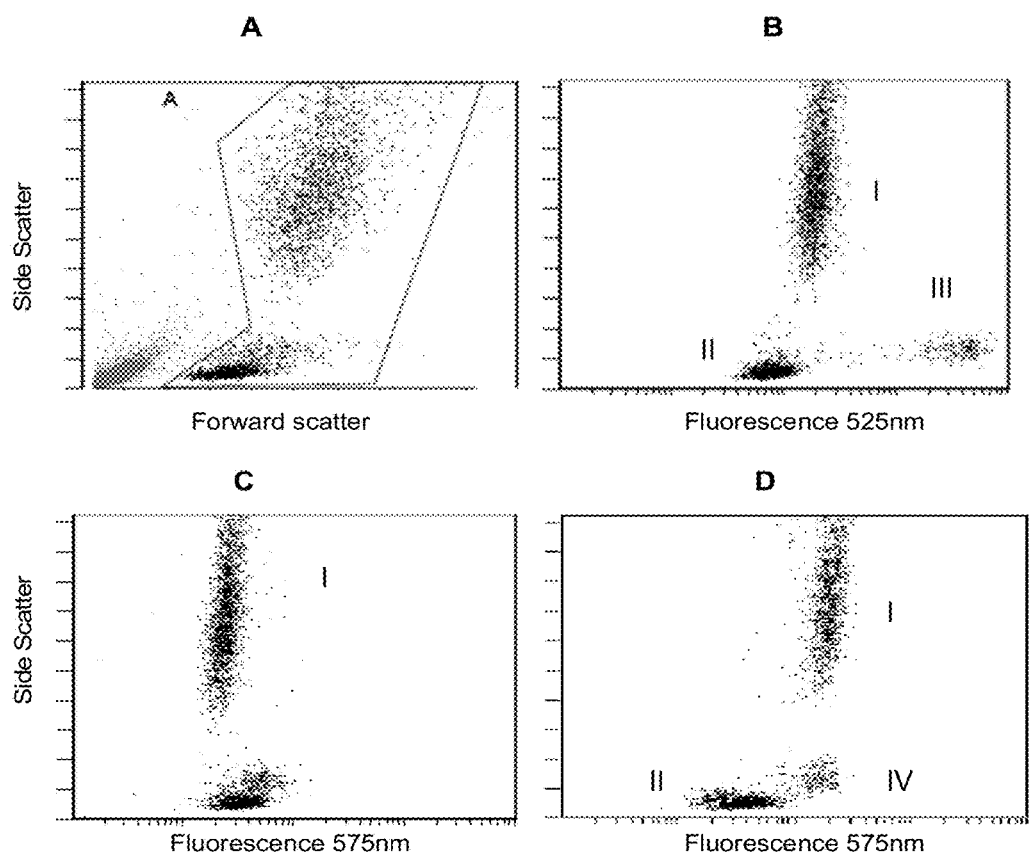

COMPOSITION FOR HIGH STRINGENCY CELL TREATMENT AND ANTIGEN RETRIEVAL

CROSS REFERENCE TO RELATED APPLICATIONS

This application claims priority to U.S. Provisional Application Ser. No. 61/747,044, filed on Dec. 28, 2012, entitled COMPOSITION FOR HIGH STRINGENCY CELL TREATMENT AND ANTIGEN RETRIEVAL, the disclosure of which is incorporated by reference herein in its entirety.

DESCRIPTION

The present invention relates to a cell treatment composition for the permeabilization of fixed blood cells, to the use of said cell treatment composition and to a method for treating a biological sample comprising fixed white blood cells for the subsequent analysis of intracellular and/or extracellular epitopes, for example phospho-epitopes. The present invention further relates to a kit comprising said cell treatment composition.

Recent developments in the analysis of cells, e.g. blood cells, have provided valuable tools for the detailed analysis of cellular structures, both within the cells and on the cell surface. The cells are usually stained with multiple labeled binding agents such as monoclonal antibodies specific for defined extracellular and/or intracellular markers in order to detect the presence of respective cellular structures and thereby to identify particular cells of interest. For example, different subsets of leukocytes are commonly differentiated by using specific cellular surface markers while various intracellular markers, e.g. cytoplasmic or nucleus associated structures, are becoming more important for studying functional characteristics of the investigated cells. The cells labeled by said specific binding agents can then be analyzed by a suitable device, preferably a flow cytometer, which is able to detect and distinguish between the various labels and other cellular properties like granularity and size.

While early applications of flow cytometry have been mainly concerned with the detection of cell surface antigens, which were readily accessible via respective antibodies, the labeling of intracellular target sites poses a greater challenge, as it requires a special pretreatment of the cells in order to make the cell membrane permeable to the respective binding agents which are specific for intracellular target sites. Such permeabilization is a critical step as the cell membrane must be made sufficiently permeable to large molecules like fluorescence-labeled antibodies. At the same time the cellular structure of the different cell populations needs to stay sufficiently conserved, so the respectively characteristic light scatter properties are maintained and cytoplasmic proteins are not lost to the extracellular space but remain localized within the cell. A fixation step is commonly used before or together with the permeabilization step to provide such stabilization. This structural conservation becomes more difficult when the conditions of conservation are more stringent, i.e. when stronger protein denaturing procedures are applied.

The required fixation reaction frequently comprises the use of aggressive reagents like e.g. formaldehyde, which can destroy or at least reduce the accessibility of surface antigens that are used for differentiating cellular subtypes via respective binding agents. Therefore some earlier methods comprised an initial step for labeling cell surface structures with respective labeled binding agents. Subsequently the cells were fixed, permeabilized and treated with different binding agents specific for intracellular targets. The so labeled cells were then detected and categorize, e.g. in a flow cytometer. However, in permeabilization procedures as they are presently used, the required components (formaldehyde, alcohol and detergent) are not compatible with each other and with the subsequent use of antibodies as binding agents. Multiple washing steps of the cells are therefore needed in order to get rid of interfering reagent residues. However, the harsh conditions of such a treatment can easily abolish the antigenic reactivity of some more sensitive cellular surface antigens which are frequently used to identify respective target populations, e.g. CD14.

In the context of cell signal transduction, proteins are often subject to reversible phosphorylation. This dynamic phosphorylation process involves competing phosphorylation and dephosphorylation reactions, and the level of phosphorylation at any given instant reflects the relative activities, at that instant, of the protein kinases and phosphatases that catalyze these reactions. Analysis of phospho-epitopes can therefore give valuable realtime insights into the regulation of signaling and metabolism processes within an individual cell. Thus, for research and diagnostic applications the analysis of the phosphorylation state of various signal transduction enzymes like phosphokinases, e.g. mitogen-activated protein kinases, is becoming more and more important. An important application of such phosphorylation studies is for example the treatment of cancer or autoimmune diseases, where the phosphorylation or dephosphorylation of certain phospho-epitopes can be indicative of the effectiveness of phosphokinase inhibitor drugs, either administered to a patient or tested in vitro.

It is well established that phospho-epitopes are generally difficult to expose (or "unmask") to respectively specific binding agents. In some cases, these epitopes are linear epitopes that may require denaturation of the protein at the epitopic site for effective antibody binding. The phospho-epitope of the phosphorylated Stat-5 protein is an example of a phospho-epitope which is especially difficult to expose. Generally very stringent denaturation conditions would be required to expose such epitopes. However, there is a significant risk that the cellular structure as well as intra- and extracellular epitopes are severely damaged by such an aggressive treatment.

According to conventional methods the detection of phospho-epitopes like p-Stat-5 requires the incubation with alcohols in order to unmask such epitopes. However alcohols may also change the cellular structure and destroy cell surface markers. Also, its use limits subsequent analysis and at least one centrifugation step is required to separate the alcohol from the treated cells.

Whenever samples comprising red blood cells, for example peripheral blood samples, are used for analysis, the lysis of these red blood cells is an important but cumbersome step. As white and red blood cells are comprised in whole blood at a ratio of about 1/1000, a preferably complete red blood cell lysis is necessary to be able to distinguish or differentiate the white blood cells.

Therefore, the technical problem underlying the present invention is to provide improved compositions, methods and kits for the treatment of fixed cells, particularly leukocytes or subclasses thereof, in order to render intracellular epitopes, such as phospho-epitopes, accessible to respectively specific binding agents while maintaining the accessibility of extracellular epitopes for corresponding binding agents. There is a need for an easy and practical method for the simultaneous analysis of extracellular targets and difficult to expose intracellular targets like certain phospho-epitopes. Preferably such a method shall be fast, easily automatable and not very labor intensive, would not require an alcohol treatment step and would allow for the use of binding agent cocktails, including binding agents directed against both intracellular and extracellular targets.

The solution to the above technical problem is achieved by the cell treatment composition for the permeabilization of fixed blood cells described herein and the embodiments characterized in the claims.

An aspect of the present invention relates to a cell treatment composition for the permeabilization of fixed blood cells, comprising an aqueous solution of
(a) at least one anionic surface active agent which is comprised in said composition in a concentration of between 0.3% and 2% (w/v), wherein a salt of said anionic surface active agent is represented by the formula (1):

Y—SO3-X+                     (1)

wherein Y is either R—O or R, and R represents an alkyl, alkylene, aryl, alkylene-alkyl, aryl-alkyl or aryl-alkylene group having 8 to 18 carbon atoms and X represents a monovalent cation, and
(b) serum albumin which is comprised in said composition in a concentration of between 0.2% and 20% (w/v), wherein the pH of said cell treatment composition is between about 2 and about 6.

According to this aspect of the invention relatively high concentrations of an anionic surface active agent are combined with a protective treatment of the cells, namely the use of serum albumin at an acidic pH value. Surprisingly it has been found that, at an acidic pH, serum albumin can bind to proteins and provide sufficient protection even against the strong denaturing effects of an elevated concentration of an anionic surface active agent. This protective effect of serum albumin was observed to be much less pronounced at higher pH values. Therefore, according to an embodiment of the invention, highly stringent denaturing conditions are used to denature and expose otherwise poorly accessible epitopes, such as certain phospho-epitopes, e.g. pStat-5, pStat-3, pStat-1, p-ERK1/2, or p-S6, while the structural integrity of the analyzed cells and their sub-cellular components is effectively protected via the simultaneous use of serum albumin at an acidic pH.

In a preferred embodiment the cell treatment composition comprises from 0.2% to 20% (w/v) of serum albumin at a pH of between 2 and 6, wherein the pH of the cell treatment composition is between 2 and 6, may be between 2.5 and 5.5, may be between 3 to 5, may be between 3.5 and 4.7, may be between 4.0 and 4.4 and is often about 4.2.

The cell treatment composition according to the present invention is especially adapted to treating fixed blood cells. The term "fixed blood cells" comprises blood cells that have been treated with a sufficient amount of a fixative, i.e. a crosslinking agent like formaldehyde, paraformaldehyde, formalin or the like in order to stabilize the overall cellular and subcellular structures. A skilled artisan is well aware of fixative agents suitable for this purpose. Without prior fixation, the cells could be severely damaged by the stringent denaturing conditions provided by the cell treatment composition of the present invention.

In a preferred embodiment the cell treatment composition is used for the permeabilization of white blood cells and the unmasking of epitopes, in particular phospho-epitopes, comprised within the white blood cells. Prior to the use of the cell treatment composition the white blood cells from a peripheral blood sample, for example, whole blood sample, are fixed by subjecting them to formaldehyde or another aldehyde comprising fixation agent in a concentration of from 2% to 6% or from 3% to 5% or preferably about 4% (w/v). The fixation does not only protect the cells against degradation but also freezes the cell in a state of phosphorylation, blocking the action of phospho-kinases and phosphorylases, which is essential for the purpose of detecting the actual activation, i.e. phosphorylation status of the analyzed phospho-epitopes. Otherwise subsequent cell treatment steps, like the labeling of intra- and/or extracellular structures of said cells with specific binding agents, could modify the activation pattern of the analyzed cells, thereby distorting the obtained results.

The cell treatment composition according to the present invention is suitable for use with fixed blood cells, in particular leukocytes (also called white blood cells) and various subclassifications of leukocytes, including but not limited to monocytes, lymphocytes, granulocytes, neutrophils, eosinophils, and basophils. The blood cells may be acquired using known techniques from either peripheral blood or tissues, particularly from mammals, including humans, mice, rats, goats, etc. The cell treatment compositions according to the present invention are especially adapted to treating fixed blood cells from human peripheral blood samples. An example of a suitable tissue derived sample is murine splenocytes.

The term "anionic surface active agent" shall also comprise anionic detergents, anionic surfactants, and anionic tensides. The anionic surface active agent comprises an anionic function group and a hydrophilic part. The anionic function group is preferably sulfate or sulfonate. The hydrophilic part preferably comprises an alkyl-group, aryl-group or alkyl-aryl group of between 8 and 18 carbon atoms.

Said anionic surface active agent is contained in the cell treatment composition in a relatively high amount of between 0.3% and 2% (w/v) and both plays a major part in the permeabilization of the cellular membrane and in the "unmasking" of intracellular epitopes. The term of "unmasking an epitope" shall indicate that the accessibility of such an "unmasked" epitope for a corresponding detectably labeled binding agent is established or at least increased as opposed to the "masked" version of the epitope. In other words the process of "unmasking" allows for the detection of cellular structures, e.g. via antibodies, that were not recognizable by said antibodies before this process.

The term "permeabilization" as used herein relates to the process of making cell membranes permeable to large molecules like antibodies and/or larger fluorophores like phycoerythrin or allophycocyanin or conjugates thereof without destroying the overall structure of said cells.

Within this application the term "epitope" shall comprise any target binding site that can be recognized by a specific binding agent such as polyclonal or monoclonal antibodies or an immunoactive fragment thereof, e.g., F(ab)'2, Fab or Fab' fragments'. A "target binding site" may be for example at least a part of a protein or at least a part of another molecule present within or on the surface of a cell. The term "specific binding agent" as used herein, shall indicate a binding agent that is capable of recognizing and binding specifically to only one or a limited number of similar epitopes while basically not recognizing and not binding to other epitopes.

Present clinical research is focused on the analysis of cellular signaling pathways and their regulation, for example in response to drug administration. Such signaling pathways comprise the activation, which is often a specific phosphorylation, of one or more defined activatable molecules, mostly signaling proteins that can be phosphorylated. Within the scope of this application the term "activatable molecule" shall describe a molecule that can be activated, i.e. switched from an inactive state to an active state, by extrinsic influence, e.g. via a phosphorylation reaction triggered by another molecule. So in one example an activatable molecule may be a cytoplasmic protein that can be phosphorylated or de-phosphorylated at specific positions.

The detection of phosphorylated molecules, e.g. phosphoproteins, is highly desired but frequently the specific phosphorylated sites of such molecules are "masked" and difficult to target via e.g. phosphorylation state specific antibodies. Prior art methods are so far not providing satisfactory solutions to this problem. The use of highly stringent cell treatment conditions, which would be required especially for the unmasking and subsequent detection of phosphor-proteins, was so far restricted by the fact that such conditions can easily destroy or severely damage the integrity of the cellular structure and the antigenic sites. Therefore the use of stringent cell treatment conditions, e.g. via employing high amounts of detergent, was not a suitable option so far.

The terms "phospho-epitope", "phosphorylated target" and "phosphorylation site" are used interchangeably herein and shall indicate a defined location of a cellular structure, preferably of an intracellular protein, that may exist in a phosphorylated and a dephosphorylated state. A "phospho-epitope" may serve as an activation state specific recognition site for specific binding agents, e.g. monoclonal antibodies, which are capable of specifically recognizing either the phosphorylated or the dephosphorylated form. By detecting the phosphorylation status of "phospho-epitopes", e.g. via flow cytometric methods, phosphorylation based cell signaling can be conveniently studied.

According to an embodiment of the invention the cell treatment composition comprises at least one salt of an anionic surface active agent selected from the group consisting of sodium dodecyl sulfate (SDS), potassium dodecyl sulfate, ammonium dodecyl sulfate and sodium dodecylbenzenesulfonate. In a preferred embodiment the anionic surface active agent comprised in the cell treatment composition is dodecyl sulfate, preferably in the form of SDS. Generally, the monovalent cation of formula (1) is preferably one or more selected from the group of $Li^+$, $Na^+$ and $K^+$ and ammonium.

In an embodiment the anionic surface active agent is represented by the formula (1), wherein R represents an alkyl, alkylene, aryl, alkylene-alkyl, aryl-alkyl or aryl-alkylene group having 10 to 18 carbon atoms. Preferably R represents an alkyl or aryl-alkyl group having 12 to 18 carbon atoms.

In a preferred embodiment the anionic surface active agent is represented by the formula (1), wherein R represents an alkyl group having 8 to 16 carbon atoms, preferably 10 to 14 carbon atoms.

In an embodiment R represents a linear or branched alkyl group. In another embodiment R comprises a benzene part and an alkyl part, wherein the alkyl part is branched or linear and covalently linked to the benzene part.

In an embodiment R comprises an alkyl, aryl or aryl-alkyl group having 12 to 18 carbon atoms, wherein one carbon atom is substituted by an atom selected from the group consisting of O, N and S.

An alkyl group is a functional group or side-chain that may be linear or branched and consists solely of single-bonded carbon and hydrogen atoms.

An aryl group is a functional group or substituent derived from an aromatic ring, for example phenyl.

An aryl-alkyl group consists of an alkyl group and an aryl group wherein the alkyl group and the aryl group are covalently linked.

In another embodiment of the invention the salt concentration of the cell treatment composition is adjusted such that a basically physiological salt concentration is attuned when a fixed biological sample and the cell treatment composition are combined. With varying sample volumes and types the salt concentration of the cell treatment composition may have to be adjusted accordingly. The ionic strength of a basically physiological salt concentration is moderate and thus provides a protective function for the cellular structures as well as for the antibodies which are used during subsequent analysis. In order to provide such a moderate ionic strength the conductivity of the cell treatment composition is preferably higher than 9 mS/cm.

In another embodiment the cell treatment composition comprises essentially no alcohol.

According to another embodiment of the invention, the pH value of the cell treatment composition is adjusted such, that when a biological sample comprising fixed white blood cells and the cell treatment composition are combined, the pH value of this combination shall be between 5 and 7 or between 5.1 and 6.8 or between 5.2 and 6.6 or between 5.3 and 6.4 or between 5.35 and 6.3 or between 5.4 and 6.2 or between 5.45 and 6.1 or between 5.5 and 6.0 or between 5.55 and 5.9 or between 5.6 and 5.8 or may be about 5.7.

Apart from the protective function of serum albumin at acidic conditions, an acidic environment also attenuates negative charges on proteins and favors hydrophobic interactions, leading to an additional fixation of the cells. In the case of the present invention, when cellular lysis is performed in the presence of an anionic detergent, the acidic condition also attenuates the negative charge of the detergent and thereby renders the detergent less aggressive.

Thus, the cell treatment composition according to this aspect of the invention advantageously is effective to lyse red blood cells, permeabilize cellular membranes and provide additional fixation of white blood cells and unmask/expose cellular epitopes, especially intracellular phospho-epitopes, in one single step.

According to an embodiment, the present invention relates to a cell treatment composition as given above, wherein said anionic surface active agent is comprised in said cell treatment composition in a concentration of between 0.3 and 2% (w/v) or in a concentration of between 0.4 and 1.9% (w/v) or in a concentration of between 0.45 and 1.8% (w/v) or in a concentration of between 0.5 and 1.7% (w/v) or in a concentration of between 0.55 and 1.6% (w/v) or in a concentration of between 0.6% and 1.5% (w/v) or in a concentration of between 0.65 and 1.4% (w/v) or in a concentration of between 0.7 and 1.3% (w/v) or in a concentration of between 0.8 and 1.2% (w/v) or in a concentration of between 0.3 and 2% (w/v) or in a concentration of between 0.9% and 1.1% (w/v) or in a concentration of about 1.0% (w/v).

As discussed above it was surprisingly found that the combined use of serum albumin at acidic conditions and an elevated concentration of an anionic surface active agent resulted in a successful cell permeabilization and a very efficient unmasking of intracellular epitopes while cellular structures remained basically conserved.

In an embodiment the cell treatment composition comprises from 0.9% to 1.3% (w/v), preferably from about 1 to 1.1% (w/v), of sodium dodecyl sulfate (SDS) as an anionic surface active agent. Such cell treatment compositions were especially effective for unmasking. In control experiments using cell treatment compositions comprising an anionic surface active agent in a concentration of more than 2% (w/v) a negative effect with regard to the stability of the cellular structure was observed.

According to an embodiment, the present invention relates to a cell treatment composition as given above, wherein said anionic surface active agent is sodium dodecyl sulfate (SDS) or sodium dodecylbenzenesulfonate (SDBS).

SDS is a very common, easily available and non-toxic detergent. While cost-efficient, SDS is a very potent detergent and ideally suited to be comprised in the present cell treatment composition used as an anionic surface active agent.

The SDS molecule comprises a highly polar part and a highly hydrophobic part. It is considered as one of the strongest protein denaturing anionic detergents. In the acidic environment of the cell treatment composition the charge and polarity of SDS are somewhat attenuated. However, the detergent will bind to the regions of interest adding negative charges to the proteins inducing their denaturation and will restore its full capacity when the cells are subsequently washed and taken up in a neutral incubation reagent as described below. Less strong anionic detergents, non-ionic detergents, zwitterionic detergents or glycosides like saponin, will add no or less negative charges in an acidic environment and will not or less efficiently denature proteins as compared to the way that SDS denatures proteins.

When SDS and serum albumin are combined at acidic conditions in the presence of elevated salt concentrations, a transitory white precipitation can be observed. Apparently, complexes of SDS and serum albumin can easily change from a state of insolubility to a state of solubility. Most probably, this is due to the easy transition of SDS from a state of aggregated micelles to a state of soluble micelles. Precipitation of these complexes in a microenvironment of cellular proteins may provide additional fixation to cellular components and to the structure of the cell as a whole. In the present invention, this additional fixation at acidic conditions is provided to white blood cells, but not to the red blood cells, which are lysed by the treatment.

While SDBS has, as compared to SDS, a similar potential to permeabilize fixed cells and to unmask phospho-epitopes contained therein, SDS seems to be having a better protective effect on sensitive surface structures like for example the CD14 antigen (see example 4).

According to a further embodiment, said anionic surface active agent of the cell treatment composition is either SDS or SDBS or a combination of SDS and SDBS, wherein the cumulative concentration of said SDS, SDBS or SDS and SDBS is between 0.3 and 2% (w/v) or between 0.4 and 1.9% (w/v) or between 0.45 and 1.8% (w/v) or between 0.5 and 1.7% (w/v) or between 0.55 and 1.6% (w/v) or between 0.6% and 1.5% (w/v) or between 0.65 and 1.4% (w/v) or between 0.7 and 1.3% (w/v) or between 0.8 and 1.2% (w/v) or between 0.3 and 2% (w/v) or between 0.9% and 1.1% (w/v) or about 1.0% (w/v).

According to an embodiment, the present invention relates to a cell treatment composition as given above, wherein said serum albumin is mammalian serum albumin, preferably bovine serum albumin.

Serum albumin is naturally present in the mammalian blood. In an embodiment, the cell treatment composition of the present invention comprises one or more selected from the group consisting of human serum albumin, bovine serum albumin, horse serum albumin or serum albumin from other mammalian sources.

Serum albumin has a protective effect with regard to cells and antigens, especially at an acidic pH (see example 5). In a further embodiment, the cell treatment composition of the present invention comprises serum albumin in a concentration of between 0.2% and 15% (w/v) or between 0.4% and 14% (w/v) or between 0.6% and 13% (w/v) or between 0.8% and 12% (w/v) or between 1.0% and 11% (w/v) or between 1.2% and 10% (w/v) or between 1.4% and 9% (w/v) or between 1.6% and 8% (w/v) or between 1.8% and 7% (w/v) or between 2.0% and 6% (w/v) or between 2.1% and 5% (w/v) or between 2.2% and 4% (w/v) or between 2.3% and 3% (w/v) or between 2.4% and 2.7% (w/v) or about or between 2.5% (w/v). A cell treatment composition comprising serum albumin in a concentration of less than 0.2% (w/v) is rather ineffective for protecting the cell structure and cellular antigens. Optimal protection will be obtained at a concentration of at least 2% (w/v) while optimal unmasking of for phospho-proteins will occur at concentrations of less than 3% (w/v). Too high concentrations of serum albumin (over 20% (w/v)) will attenuate the effect of the detergent on the unmasking of antigenic sites of the phospho-proteins.

According to a preferred embodiment the concentration of the serum albumin concentration comprised in the cell treatment composition is adjusted thus, that in the resulting mixture of step (b) the combined serum albumin concentration of the mammalian serum albumin comprised in the analyzed mammalian biological sample and the added serum albumin, e.g. bovine serum albumin, added via the cell treatment composition of the present invention in step (b), is between 0.2% and 15% (w/v) or between 0.4% and 14% (w/v) or between 0.6% and 13% (w/v) or between 0.8% and 12% (w/v) or between 1.0% and 11% (w/v) or between 1.2% and 10% (w/v) or between 1.4% and 9% (w/v) or between 1.6% and 8% (w/v) or between 1.8% and 7% (w/v) or between 2.0% and 6% (w/v) or between 2.1% and 5% (w/v) or between 2.2% and 4% (w/v) or between 2.3% and 3% (w/v) or between 2.4% and 2.7% (w/v) or about or between 2.5% (w/v). The pH of said mixture shall be between 5 and 7 or between 5.1 and 6.8 or between 5.2 and 6.6 or between 5.3 and 6.4 or between 5.35 and 6.3 or between 5.4 and 6.2 or between 5.45 and 6.1 or between 5.5 and 6.0 or between 5.55 and 5.9 or between 5.6 and 5.8 or may be about 5.7. In a preferred embodiment, the acidic serum albumin of said mixture is buffered by serum albumin itself and preferably also by the addition of a small quantity of phosphate, wherein the phosphate is comprised in the mixture in a concentration of less than 20 mM or less than 16 mM or less than 12 mM or less than 9 mM or less than 6 mM or less than 4 mM or about 2 mM.

According to an embodiment, the present invention relates to a cell treatment composition as given above, wherein the pH of said treatment composition is between 3 and 5.5. According to a further embodiment, the pH of the cell treatment composition according to the present invention is between 3.8 and 4.6, preferably around 4.2.

Preferably the pH of the cell treatment composition should be between 2 and 6 or between 2.3 and 5.8 or between 2.6 and 5.6 or between 2.9 and 5.4 or between 3.2 and 5.2 or between 3.4 and 5.0 or between 3.6 and 4.9 or between 3.7 and 4.7 or between 3.8 and 4.6 or between 3.9 and 4.5 or between 4.0 and 4.4 or between 4.1 and 4.3 or about 4.2.

According to an embodiment, the present invention relates to a cell treatment composition as given above, wherein said treatment composition further comprises a chaotropic salt.

The term "chaotropic salt" shall indicate a substance which is capable of denaturing macromolecules such as proteins and nucleic acids, thereby disrupting their structure. Chaotropic salts can also negatively influence the stability of cell membranes by disrupting the hydrophobic regions of their lipid bilayers. Above a certain concentration, this effect can ultimately lead to cell lysis.

In an embodiment of the invention the cell treatment composition comprises one or more selected from the group consisting of chloride salts, iodide salts and perchlorate salts. In an embodiment the cell treatment composition comprises one or more selected from the group consisting of magnesium chloride, guanidinium chloride, sodium iodide, lithium perchlorate and sodium thiocyanate. In a preferred embodiment the chaotropic salt comprised in the cell treatment composition is either perchlorate or thiocyanate or a combination thereof. It has been found that these chaotropic salts are especially suitable within the scope of the present invention due to their capacity to decrease the pH locally in macromolecules.

The chaotropic salt(s) advantageously provide additional denaturation potential to the SDS. In a preferred embodiment the cell treatment composition comprises a chaotropic salt selected from the group consisting of a salt of perchlorate and of a salt of thiocyanate. The chaotropic salts of perchlorate and thiocyanate are specifically effective in unmasking phospho-epitopes like p-Stat5. Further the red blood cell lysis of the fixed blood is enhanced by both perchlorate and thiocyanate. It is preferred to use a cell treatment composition comprising perchlorate and/or thiocyanate instead of increasing the stringency, i.e. the denaturation potential, of the cell treatment composition by just raising the concentration of the anionic surface active agent contained therein. At overly high concentrations of the anionic surface active agent there is an increasing risk, that cell structures will become damaged. Thus it seems as if the chaotropic effect of perchlorate or thiocyanate is complementary to the function of the anionic surface active agent, e.g. SDS, and that it is more specific to the unmasking of the phospho-epitopes like e.g. the p-Stat 5 epitope.

In a further embodiment the cell treatment composition comprises a chaotropic salt in a concentration of between 20 mM and 250 mM or between 50 mM and 230 mM or between 80 mM and 210 mM or between 110 mM and 190 mM or between 130 mM and 170 mM or about 150 mM. A chaotropic salt concentration of more than 250 mM may have detrimental effects on the integrity of the analyzed cells.

In an embodiment the cell treatment composition of this invention comprises perchlorate and/or thiocyanate individually or in a combination in a cumulative concentration of between 20 mM and 250 mM or between 50 mM and 230 mM or between 80 mM and 210 mM or between 110 mM and 190 mM or between 130 mM and 170 mM or about 150 mM. At these concentrations the integrity of the treated cell membranes is destabilized in a controlled manner, thereby assisting in the permeabilization of the cells membranes. Also such concentrations which are close to the approximate value of an iso-osmotic solution, the unfolding of phosphorylated proteins like p-Stat5 is facilitated.

According to an embodiment, the present invention relates to a combination comprising a cell treatment composition as described above and a biological sample comprising fixed white blood cells, wherein said combination has a pH value of between 5.5 and 7.

In an embodiment the combination comprises a cell treatment composition as described above and a biological sample comprising fixed white blood cells selected from the group consisting of a whole blood sample, a sample comprising isolated subpopulations of leukocytes and a bone marrow sample. In a preferred embodiment the biological sample is a whole blood sample, optionally treated with an anticoagulant like ethylenediamine tetraacetic acid (EDTA), and of mammalian, preferably of human origin.

In a preferred embodiment the combination comprises 1000 µl of a cell treatment composition as described above and 100 to 400 µl, preferably 160 to 250 µl and most preferred about 200 µl of a biological sample comprising fixed white blood cells, wherein said combination has a pH value of between 5.5 and 7, preferably a pH of about 5.6 to 6 and most preferred a pH of 5.7.

The term "white blood cell" comprises all kinds of leukocytes, including lymphocytes, monocytes and granulocytes. This invention is applicable to all leukocytes that comprise intracellular activatable phosphor-proteins, which may be unmasked by using the cell treatment composition and the related methods according to the present invention.

In an embodiment the biological sample comprises fixed lymphocytes. In another embodiment the biological sample comprises fixed monocytes. In yet another embodiment the biological sample comprises fixed granulocytes.

According to another embodiment, the present invention relates to the use of a cell treatment composition as described above for the treatment of an isolated biological sample comprising fixed white blood cells.

According to a preferred embodiment the invention relates to the use of a cell treatment composition as described above for the permeabilization of fixed white blood cells comprised in an isolated biological sample, preferably a whole blood sample. According to an embodiment the fixed white blood cells were obtained by treating a whole blood sample with a one or more fixatives selected from the group of formaldehyde, paraformaldehyde and formalin. Preferably about 100 µl of a whole blood sample are fixed by addition of 60 µl of a formaldehyde solution (10% (w/v)).

According to another embodiment the invention relates to the use of a cell treatment composition as described above for the permeabilization of fixed white blood cells comprised in an isolated biological sample, preferably a whole blood sample, and for the lysis of red blood cells comprised in the isolated biological sample.

According to a preferred embodiment the invention further relates to the use of a cell treatment composition as described above for the permeabilization of fixed white blood cells comprised in an isolated biological sample, preferably a whole blood sample, and for the lysis of red blood cells comprised in the isolated biological sample and for the additional stabilization of the fixed white blood cells and for the unmasking of intracellular epitopes comprised in the fixed white blood cells.

According to a preferred embodiment the invention further relates to the use of a cell treatment composition as described above for the simultaneous permeabilization of fixed white blood cell, the lysis of red blood cells, the unmasking of intracellular epitopes comprised in the fixed while blood cells and an for the additional stabilization of the fixed white blood cells in a single step, wherein the cell surface epitopes of the fixed white blood cells are largely conserved during these uses of the cell treatment composition.

According to a further embodiment the invention further relates to the use of a cell treatment composition as described above, wherein essentially no alcohol is comprised in said cell treatment composition.

Also according to an embodiment of the invention less centrifugation steps are needed as in current procedures which require alcohol treatment. Therefore the methods of the invention are easier and quicker to perform as compared to such conventional methods.

The present invention further relates to the use of a cell treatment composition wherein the fixed white blood cells are permeabilized by means of a cell treatment composition as described above and labeled by means of at least one detectably labeled binding agent specific for an intracellular and/or extracellular epitope.

In an embodiment the fixed white blood cells are labeled with at least one detectably labeled binding agent selected from the group consisting of a polyclonal antibody, or monoclonal antibody or an immunoactive fragment thereof, wherein the at least one detectably labeled binding agent is labeled with a detectable label, preferably a fluorescence label, which makes it possible to identify said binding agent via a suitable detection technology, for example to detect a fluorescence label via fluorescence flow cytometry. In an embodiment of the invention the detectable labels of the at least one binding agent are selected from one or more of the group consisting of fluorescent labels, labels consisting of non-fluorescent chromophores, Raman spectroscopy labels, radioactive labels and labels suitable for mass spectrometric detection.

In a preferred embodiment at least two, preferably all of the detectable labels shall be distinguishable from other employed detectable labels, so that by detecting a label an unambiguous identification of the corresponding binding agent and ultimately the corresponding antigenic structure addressed by said binding agent is possible.

An embodiment of the invention relates to the use of a cell treatment composition wherein the fixed white blood cells are labeled with at least one detectably labeled binding agent specific for an intracellular epitope and at least one detectably labeled binding agent specific for an extracellular epitope. Preferably multiple detectably labeled binding agents specific for an intracellular epitope and multiple detectably labeled binding agents specific for an extracellular epitope are used.

Example detectably labeled binding agents include without limitation the following antibodies: Mouse anti-Stat5 (pY694)-PE (BD Biosciences Pharmingen San Jose Calif.), Mouse Phospho-p44/42 MAPK (Erk1/2) (Thr202/Tyr204) (E10) Alexa Fluor® 647 (Cell Signaling Technology Inc., Danvers, Mass.), Phospho-p38 MAPK (T180/Y182) Alexa Fluor® 488. (Cell Signaling Technology Inc., Danvers, Mass.), Phospho-Stat1 (Tyr701) (58D6) Alexa Fluor® 488. (Cell Signaling Technology Inc., Danvers, Mass.), Phospho-Stat3 (Tyr705) (3E2) Alexa Fluor® 488. (Cell Signaling Technology Inc., Danvers, Mass.), Phospho-Akt (Ser473) (Beckman Coulter Inc., Brea, Calif., product No. A88915), Phospho-p44/42 MAPK (Erk1/2) (Thr202/Tyr204) (Beckman Coulter Inc. product No. A88921), Phospho-Stat3 (Tyr705) (Beckman Coulter Inc., Brea, Calif., product No. A88925), Phospho-p38 MAPK (Thr180/Tyr182) (Beckman Coulter Inc., Brea, Calif., product No. A88933), Phospho-S6 Ribosomal Protein (Ser235/236) (Beckman Coulter Inc., Brea, Calif., product No. A88936), Phospho-Stat1 (Tyr701) (Beckman Coulter Inc., Brea, Calif., product No. A88941), Phospho-SAPK/JNK (Thr183/Tyr185) (Beckman Coulter Inc., Brea, Calif., product No. A88944).

In another embodiment the invention further relates to the use of a cell treatment composition wherein fixed white blood cells are labeled by means of at least one detectably labeled binding agent which is specific for a phospho-epitope, preferably an intracellular phospho-epitope, either in the phosphorylated or the de-phosphorylated state. In a preferred embodiment a detectably labeled binding agent specific for Stat-5, preferably in its phosphorylated form, is used.

According to one embodiment of the invention the detectably labeled binding agent(s) are provided separately and added to a combination of a biological sample comprising fixed white blood cells and a cell treatment composition according to the present invention. According to another embodiment of the invention the detectably labeled binding agent(s) are first combined with the cell treatment composition according to the present invention. Subsequently the obtained combination of detectably labeled binding agent(s) and the cell treatment composition is added to a biological sample comprising fixed white blood cells.

According to an embodiment the invention relates to the use of a cell treatment composition as described above for preparing permeabilized white blood cells with at least partially exposed intracellular phospho-epitopes for subsequent labeling with detectably labeled binding agents and analysis in a flow cytometry device, preferably a fluorescence flow cytometry device.

In an embodiment the invention relates to the use of a cell treatment composition for unmasking intracellular epitopes, preferably at least one phospho-epitope, wherein no alcohol treatment of the fixed white blood cells is required for the unmasking of said epitope(s). It is advantageous to avoid the use of alcohols, because alcohols may interfere with other assay reagents, cellular surface markers may be destroyed by the alcohol and additional centrifugation steps would be required in order to separate the treated cells again from the alcohol prior to analysis.

A further aspect of the present invention relates to a method for treating an isolated biological sample, said sample comprising at least white blood cells, comprising the steps of:
(a) a fixation step comprising contacting said biological sample with a fixative, wherein said fixative is added in a sufficient amount to achieve at least partial cross-linking of proteins, lipoproteins and nucleic acid molecules;
(b) a permeabilization step, subsequent to step (a), comprising contacting said biological sample with the cell treatment composition according to the present invention.

According to an embodiment the invention relates to a method for treating an isolated biological sample by subjecting it to a fixation step and subsequently subjecting it to a permeabilization step in order to prepare said biological sample for the cytometric analysis of intracellular and/or extracellular epitopes, preferably via a flow cytometer. Preferably both at least one intracellular and at least one extracellular epitope is labeled with respectively specific binding agents and subsequently analyzed in a cytometer device.

According to an embodiment the fixation step (a) comprises the contacting of a biological sample comprising at least white blood cells with a sufficient amount of a fixative (fixation reagent) to achieve at least partial cross-linking of the proteins, lipoproteins and nucleic acid molecules of said white blood cells, whereby fixed white blood cells are obtained, which are structurally conserved. In this context the term "sufficient amount" shall mean, that the concentration of the fixative is selected such that, when the fixative an the biological sample are combined, the resulting fixative concentration is effective to stabilize the white blood cells in order to avoid in the subsequent permeabilization step (b) a destruction of these cells or a loss of cytoplasmic molecules through the permeabilized cellular membrane.

Preferably an aldehyde based fixative like formaldehyde, paraformaldehyde or the like is used. According to an embodiment the fixative is mixed with the biological sample comprising at least white blood cells in such a ratio that the resulting mixture comprises from 1% to 10% (w/v) or from 1% to 10% (w/v) or from 1.5% to 9% (w/v) or from 2% to 8% (w/v) or from 2.5% to 7% (w/v) or from 3% to 6% (w/v) or from 3.5% to 5% (w/v) or about 4% (w/v) of the fixative, e.g. formaldehyde. According to a preferred embodiment step (a) comprises contacting 50 to 150 µl, preferably about 100 µl, of a whole blood sample with about 30 µl to 90 µl, preferably about 60 µl, of a 10% Formaldehyde solution.

According to an embodiment the method for treating an isolated biological sample comprises a permeabilization step, subsequent to step (a), comprising contacting the biological sample with the cell treatment composition according to the present invention for permeabilizing the fixed white blood cells contained in the biological sample and for unmasking intracellular epitopes, preferably phospho-epitopes, comprised in the fixed white cells, and thereby preparing the cells for the subsequent analysis of intracellular and/or extracellular epitopes.

The expression "step Y, subsequent to step X" is used within this application to indicate that a step Y is performed chronologically after step X, either directly thereafter or after one or more other steps which follow step X.

In an embodiment the method of the invention further comprises an activation step (x), wherein the activation step (x) comprises the addition of an activator reagent to an isolated biological sample comprising white blood cells, wherein the activation reagent is adapted to trigger/activate at least one signal transduction pathway within the white blood cells comprised in the biological sample. For example, without limitation, suitable activator reagents may be one or more selected from the group consisting of Lipopolysaccharide (LPS), CD40L, phorbol 12-myristate 13-acetate (PMA), Transforming growth factor (TGF), Toll-like receptor 4 (TLR4) and Tumor necrosis factor (TNF-alpha).

In an embodiment the method of the invention further comprises a cell surface labeling step (y) prior to or concurrently with step (b), wherein the cell surface labeling step (y) comprises the addition of at least one detectably labeled binding agent specific for an extracellular epitope. For example, without limitation, suitable extracellular epitopes may be one or more selected from the group consisting of CD-3, CD-4, CD-8, CD-14, CD-15, CD-19 and CD-45. Preferably step (y) comprises the addition of multiple detectably labeled binding agents specific for an extracellular epitope.

According to a preferred embodiment of the method of the invention a whole blood sample is combined with a fixation reagent, preferably a 10% formaldehyde solution, according to step (a), wherein the volume of the fixation reagent is from about 40% to 80%, preferably about 60% of the volume of the whole blood sample. Optionally an activator reagent according to step (x) and optionally at least one detectably labeled binding agent specific for an extracellular epitope according to step (y) are added to the biological sample, wherein the added volume of the activator reagent is from about 0.5% to 10%, preferably about 1% of the volume of the whole blood sample and the added volume of each detectably labeled binding agent is from about 5% to 40%, preferably about 20% of the volume of the whole blood sample.

To permit the entrance of the serum albumin comprised in the cell treatment composition into the cells, about 0.3%-2% (w/v) of an anionic surface active agent are comprised in the cell treatment composition of the present invention. According to an embodiment of the invention the biological sample is contacted in step (b) with a cell treatment composition comprising either SDS or SDBS or a combination of SDS and SDBS at a cumulative concentration of from 0.7% to 1.5% (w/v), preferably from 1% to 1.1% (w/v). The protection by the acidic serum albumin is provided to the white blood cells, but not to the red blood cells, which are therefore lysed by the cell treatment composition.

According to an embodiment the permeabilization step (b) is also effective to expose intracellular epitopes, preferably phospho-epitopes, and making them accessible ("unmasking" them) for subsequent detection by respectively specific binding agents, e.g. monoclonal antibodies. An example of a potential phospho-epitope of interest is the p-Stat5 epitope which is known to be generally difficult to expose.

In an embodiment of the invention step (b) comprises the unmasking of at least one intracellular epitope, which may be present within the cell in a phosphorylated and a de-phosphorylated state. Preferably multiple intracellular epitopes are unmasked in step (b) of the present invention.

According to another embodiment of the invention the methods of the invention do not require an alcohol step in order to unmask intracellular antigens of interest. The cell treatment composition according to the invention, which is described above in more detail, allows for the replacement of alcohols by different, more gentle agents, and therefore facilitates thorough unmasking of intracellular epitopes while preserving susceptible cellular structures, like e.g. the cellular surface antigen CD14, which are not compatible with the use of alcohol.

According to an embodiment the methods of the invention are adapted to treat a biological sample, preferably a whole blood sample, in order to prepare fixed and permeabilized white blood cells with unmasked intracellular epitopes, preferably epitopes of activatable intracellular molecules like e.g. phospho-proteins, for the subsequent detection of the activation state of said molecules. According to this embodiment, detectably labeled activation state specific binding agents are allowed to bind to the respective intracellular targets and are subsequently detected, preferably via flow cytometry.

In an embodiment, the method of the invention does not require a wash/centrifugation step of the fixed cells subsequent to the fixation step (a) and prior to the permeabilization step (b). The employed fixative is neutralized by the cell treatment composition and poses no problem for subsequent method steps. In an embodiment of the invention the method for treating a biological sample comprises only a single centrifugation/washing step, namely directly after the permeabilization step (b). Any other centrifugation/washing steps that were required in conventional methods for preparing white blood cells for the flow cytometric analysis of extracellular and intracellular target structures, preferably phosphorylated proteins, are no longer required according to this embodiment of the invention.

In an embodiment the present invention further relates to a method for treating a biological sample, said sample comprising at least white blood cells, in order to prepare said biological sample for the subsequent analysis of intracellular and/or extracellular epitopes comprising the steps of:
- (a) a fixation step comprising contacting said biological sample with a fixative, wherein said fixative is added in a sufficient amount to achieve at least partial cross-linking of proteins, lipoproteins and nucleic acid molecules;
- (b) a permeabilization step, subsequent to step (a), comprising contacting said biological sample with a cell treatment composition according to the present invention, and
- (c) a labeling step, subsequent to step (b), comprising contacting said biological sample with at least one detectably labeled binding agent specific for an intracellular and/or an extracellular epitope.

After the permeabilization step (b), i.e. after the permeabilization of the fixed cells comprised in the biological sample, at least one detectable binding agent, preferably a fluorescently labeled antibody, is brought into contact with said biological sample.

In a preferred embodiment at least one detectable binding agent directed against a cell surface antigen and at least one detectable binding agent directed against an intracellular antigen are used in labeling step (c). The detectable binding agents may be added jointly in form of a mixture of at least two binding agents or separately.

In an embodiment, the method further comprises a centrifugation step prior to step (c) for separating the fixed and permeabilized white blood cells from residual reagent components of preceding steps and cell debris. Such a centrifugation step is especially beneficial when a whole blood sample was used as the biological sample. The cellular pellet, after the removal of the supernatant, is taken up in a suitable incubation reagent in which the antibody reaction takes place.

In a further embodiment the binding agent(s) are added to the biological sample after step (b) together with or separate from a suitable incubation reagent. Preferably the employed detectable binding agent(s) are added to the biological sample simultaneously with the addition of said incubation reagent or thereafter.

The invention also relates to an incubation reagent comprising a buffering substances with a pKa in the neutral pH range (e.g HEPES or another 'Good Buffer' selected from the group consisting of MES, ADA, PIPES, ACES, Cholamine chloride, BES, TES, Acetamidoglycine, Tricine, Glycinamide, Bicine) in a concentration range from 1 to 50 mM, preferably 10 mM, bovine or other mammalian serum albumin in a concentration range from 0.2 to 20%, preferably 4% (w/v), sodium perchlorate or sodium thiocyanate in a concentration range from 50 to 250 mM, preferably from 100 to 160 mM and most preferred about 120 mM, optionally calcium chloride in a concentration of 5 mM or less, preferably 1 mM and Proclin® 300 or a comparable preservative in a concentration range from 0.01 to 0.2%, preferably 0.05% (v/v). The pH of the incubation reagent of the invention is adjusted to a value of from 6 to 9 or from 6.3 to 8.7 or from 6.5 to 8.5 or from 6.7 to 8.3 or from 6.9 to 8.1 or from 7.1 to 7.9 or from 7.3 to 7.7 or to about 7.5 using preferably sodium hydroxide. An exemplary suitable composition of an incubation reagent according to the invention is given in example 1.

In an embodiment the present invention further relates to a method for treating a biological sample, said sample comprising at least white blood cells, in order to prepare said biological sample for the subsequent analysis of intracellular and/or extracellular epitopes comprising the steps of:
- (a) a fixation step comprising contacting said biological sample with a fixative, wherein said fixative is added in a sufficient amount to achieve at least partial cross-linking of proteins, lipoproteins and nucleic acid molecules;
- (a1) an incubation step, subsequent to step (a), comprising an incubation of said biological sample at a temperature of between 15° C. and 30° C., wherein said sample is preferably incubated for between 5 and 15 minutes;
- (b) a permeabilization step, subsequent to step (a), comprising contacting said biological sample with a cell treatment composition according to the present invention, and
- (c) optionally a labeling step, subsequent to step (b), comprising contacting said biological sample with at least one detectably labeled binding agent specific for an intracellular and/or an extracellular epitope.

During incubation step (a1) the biological sample as obtained in step (a) is allowed to rest for about 5 to about 15 minutes, so a preferably complete fixation of the cells can be obtained. With shorter incubation times the fixation reaction may be incomplete while incubation times extended beyond 15 minutes may lead to an over-fixation, thus rendering the unmasking of intracellular epitopes more challenging. Best results will be obtained for incubation periods of between about 8 to about 12 minutes.

In a preferred embodiment step (a1) comprises an incubation of between 8 to 12 minutes at a temperature in the range from about 15 to about 30 degree Celsius, preferably in the range from about 20 to about 25 degree Celsius. It is understood, that the required incubation time will be to some extend reduced, when a higher incubation temperature is used, and vice versa.

Thorough mixing during incubation step (a1) should be avoided in order to avoid damage to the cells. Instead, gentle mixing or pivoting of the test tubes containing the treated biological samples, e.g. by hand or on a simple roller rocker, is preferred.

In an embodiment the present invention further relates to a method for treating a biological sample, said sample comprising at least white blood cells, in order to prepare said biological sample for the subsequent analysis of intracellular and/or extracellular epitopes comprising the steps of:
- (a) a fixation step comprising contacting said biological sample with a fixative, wherein said fixative is added in a sufficient amount to achieve at least partial cross-linking of proteins, lipoproteins and nucleic acid molecules;
- (a1) optionally an incubation step, subsequent to step (a), comprising an incubation of said biological sample at a temperature of between 15° C. and 30° C., wherein said sample is preferably incubated for between 5 and 15 minutes;
- (b) a permeabilization step, subsequent to step (a), comprising contacting said biological sample with a cell treatment composition according to the present invention;
- (b1) an incubation step, subsequent to step (b), comprising an incubation of said biological sample at a temperature of between 20° C. and 50° C., wherein said sample is preferably incubated for between 2 and 10 minutes and
- (c) optionally a labeling step, subsequent to step (b) or (b1), comprising contacting said biological sample with at least one detectably labeled binding agent specific for an intracellular and/or an extracellular epitope.

The incubation step (b1) shall assure that the fixed white blood cells undergo a most consistent and thorough permeabilization reaction. The temperature of this step should be between 20 and 50° C., preferably between about 30° C. and 45° C. and most preferred at about 37° C. At this temperature an incubation time of 2 to 10 minutes, preferably 3 to 7 minutes and most preferred about 5 minutes is suitable. A shorter incubation time as well as the use of incubation temperatures below 20° C. may lead to reduced permeabilization efficiency, and a too low temperature during the permeabilization reaction will diminish the hydrophobic interactions between the detergent and the target epitopes. Therefore, especially for certain epitopes needing a strong hydrophobic interaction, like p-Stat5, a temperature of around 37° C. is recommended.

On the other hand, incubation temperatures above 50° C. and a prolonged incubation of more than 10 minutes could result in denaturation and precipitation of cellular and serum proteins.

In a preferred embodiment an incubation temperature of 37° C. is maintained in step (b1) for about 5 minutes.

In an embodiment the present invention further relates to a method for treating a biological sample, said sample comprising at least white blood cells, in order to prepare said biological sample for the subsequent analysis of intracellular and/or extracellular epitopes comprising the steps of:
- (a) a fixation step comprising contacting said biological sample with a fixative, wherein said fixative is added in a sufficient amount to achieve at least partial cross-linking of proteins, lipoproteins and nucleic acid molecules;
- (a1) optionally an incubation step, subsequent to step (a), comprising an incubation of said biological sample at a temperature of between 15° C. and 30° C., wherein said sample is preferably incubated for between 5 and 15 minutes;
- (b) a permeabilization step, subsequent to step (a), comprising contacting said biological sample with a cell treatment composition according to the present invention;
- (b1) optionally an incubation step, subsequent to step (b), comprising an incubation of said biological sample at a temperature of between 20° C. and 50° C., wherein said sample is preferably incubated for between 2 and 10 minutes;
- (b2) a washing step, subsequent to step (b) or (b1) and
- (c) optionally a labeling step, subsequent to step (b1), comprising contacting said biological sample with at least one detectably labeled binding agent specific for an intracellular and/or an extracellular epitope.

The washing step (b2) is adapted to purify the fixed and permeabilized cells from reagent components present in the products of step (b) or (b1) that could interfere with the subsequent labeling step (c). Hence, in an embodiment of the invention, the washing step (b2) is performed subsequently to step (b) or (b1) and before step (c).

The term "washing" step shall be interpreted in the sense of "purification" step and shall comprise known cell purification techniques like dialysis, centrifugation or other suitable methods. Preferably, the washing step (b2) is carried out by subjecting the cellular reaction mixture obtained in step (b) or (b1) to a centrifugation force sufficient for pelleting the cells, preferably about 300 g for about 5 minutes. Subsequently the supernatant is discarded and the pellet is taken up in an incubation reagent. The serum albumin contained in the incubation reagent is effective to neutralize potentially remaining residues of the anionic surface active agent, e.g. SDS, and the fixative, e.g. formaldehyde, both capable of hampering the immune reaction. According to an embodiment of the invention the incubation reagent contains sodium perchlorate or thiocyanate or a mixture thereof at a physiological concentration. The use of sodium perchlorate and/or thiocyanate at this concentration basically prevents that already unmasked epitopes, especially phospho-epitopes, revert to a masked status during the incubation reaction.

In an embodiment the present invention further relates to a method for treating a biological sample, said sample comprising at least white blood cells, in order to prepare said biological sample for the subsequent analysis of intracellular and/or extracellular epitopes comprising the steps of:
- (a) a fixation step comprising contacting said biological sample with a fixative, wherein said fixative is added in a sufficient amount to achieve at least partial cross-linking of proteins, lipoproteins and nucleic acid molecules;
- (a1) optionally an incubation step, subsequent to step (a), comprising an incubation of said biological sample at a temperature of between 15° C. and 30° C., wherein said sample is preferably incubated for between 5 and 15 minutes;
- (b) a permeabilization step, subsequent to step (a), comprising contacting said biological sample with a cell treatment composition according to the present invention;
- (b1) optionally an incubation step, subsequent to step (b), comprising an incubation of said biological sample at a temperature of between 20° C. and 50° C., wherein said sample is preferably incubated for between 2 and 10 minutes;
- (b2) a washing step, subsequent to step (b) or (b1) and
- (c) a labeling step, subsequent to step (b1), comprising contacting said biological sample with at least one detectably labeled binding agent specific for an intracellular and/or an extracellular epitope.
- (c1) a dilution step, subsequent to step (c), comprising contacting said biological sample with a washing composition.

According to an embodiment of the invention an optional incubation step may be performed after the labeling step (c). The optional incubation step comprises an incubation of from 5 to 25 minutes, preferably from 10 to 20 minutes and most preferred of about 15 minutes at room temperature. This optional incubation step is fostering a thorough labeling of said intracellular and/or extracellular epitopes.

Subsequently, the reaction mixture resulting from step (c) is taken up in a washing composition according to step (c1) in a ratio of from 1:5 to 1:15, preferably in a ratio of from 1:10.

The invention further relates to a washing composition comprising Phosphate buffered saline (PBS, potassium free) or another physiological washing medium, formaldehyde solution (37%) in a concentration range from 0.1 to 2%, preferably 0.5% (v/v), non-ionic surfactant, such as PLURONIC F68 (Life Technologies, Carlsbad, Calif.) in a concentration range from 0.01 to 1%, preferably 0.1% (v/v) and sodium lauroyl sarcosinate in a concentration range from 0.005% to 0.5%, preferably 0.05% (v/v). The pH of the washing composition is adjusted to 7.0 to 7.5, preferably to 7.2 using sodium hydroxide or hydrochloric acid. The formaldehyde comprised in the washing composition ensures that the sample is sufficiently conserved before analysis. A non-ionic surfactant, such as PLURONIC F68 (Life Technologies, Carlsbad, CA) and lauroyl sarcosinate are added to the washing composition in order to prevent the cells from sticking to other cells and to the tubing of an employed cytometer device.

In another embodiment the biological sample is first centrifuged in order to remove excess antibody. Subsequently the pellet is taken up in 50 to 200 µl, preferably about 100 µl of washing composition. The sample then can be analyzed on a cytometer.

In a further embodiment of the invention said at least one detectably labeled binding agent, preferably labeled with a fluorescent label, is specific for a phosphorylated protein, e.g. p-Stat-5. The detection of said at least one detectably labeled binding agent can be performed via flow cytometry.

In an embodiment of the invention, extracellular epitopes specific for leucocyte subpopulations and intracellular phosphorylated proteins are detected by means of the methods according to the invention. Preferably only one centrifugation/washing step, directly preceding step (c) is used during the complete cell treatment procedure prior to the analysis of the treated sample on a flow cytometry device.

A further aspect of the present invention relates to a kit comprising
- a) a cell treatment composition according to the present invention.
- b) an incubation reagent comprising serum albumin and perchlorate,
- c) at least one detectably labeled binding agent specific for an intracellular epitope, and
- d) at least one detectably labeled binding agent specific for an extracellular epitope.

In a preferred embodiment the kit comprises a cell treatment composition according to the present invention, an incubation reagent according to the present invention, a detectably labeled binding agent specific for an intracellular epitope, preferably a phospho-epitope and a detectably labeled binding agent specific for an extracellular epitope suitable for the identification of white blood cells. In another embodiment the kit further comprises a fixation reagent comprising preferably formaldehyde or paraformaldehyde in a concentration of between 1% and 37% (w/v) or between 2% and 33% (w/v) or between 3% and 37% (w/v) or between 4% and 30% (w/v) or between 5% and 25% (w/v) or between 6% and 20% (w/v) or between 7% and 15% (w/v) or between 8% and 12% (w/v) or between 9% and 11% (w/v) or about 10% (w/v).

According to an embodiment at least one of the detectably labeled binding agents is a fluorescently labeled antibody directed against an activatable epitope, preferably a phospho-epitope, that may be present within a biological cell in a phosphorylated and in a dephosphorylated form, wherein said fluorescently labeled antibody is capable of detecting either the phosphorylated or the dephosphorylated form of said phospho-epitope specifically.

The incubation reagent according to the invention is adapted to avoid damage to both intra- and extracellular epitopes and to allow for the specific binding of at least one detectably labeled binding agent to its corresponding epitopes. For example, a suitable incubation reagent comprises 4% of serum albumin in HEPES buffered perchlorate at physiological strength. The serum albumin, preferably, BSA is useful for the absorption of residues of SDS and formaldehyde, which could interfere with the antibody reaction. To prevent the closure of exposed antigens the salt providing the physiological conditions is a suitable chaotropic salt, for example sodium perchlorate or thiocyanate.

Better labeling properties of phospho-proteins in terms of higher signal to noise ratios were observed if perchlorate was used at physiological concentration in the incubation reagent. In this way, the chaotropic effect of the perchlorate salt was extended from the lysis reagent into the incubation reagent, without hampering the labeling of cell surface proteins.

According to a preferred embodiment the fixation reagent comprised in the kits of the invention and used in the methods of the invention for the fixation of a biological sample comprising white blood cells, preferably a whole blood sample, comprises in an aqueous solution 150 mM sodium chloride and 10% (w/v) formaldehyde (methanol-free). It is understood that a plurality of different, e.g. commercially available fixation buffers comprising a similar amount of formaldehyde or a comparable aldehyde comprising fixation agent are equally suited to be comprised in the kits of the invention and can be used in the methods of the invention. Likewise the above mentioned uses of the cell treatment composition of the present invention are not limited to this specific embodiment of the fixation reagent.

According to a preferred embodiment the cell treatment composition comprised in the kits of the invention and used in the methods of the invention comprises in an aqueous solution 34.7 mM sodium dodecyl sulfate, 1% (w/v) Bovine serum albumin (BSA) 1% (w/v), optionally 2 mM sodium dihydrogen phosphate, optionally 150 mM sodium perchlorate and optionally 0.05% (v/v) Proclin® 300. The final pH of the cell treatment composition is adjusted to 4.2 by the addition of NaOH.

According to a preferred embodiment the incubation reagent comprised in the kits of the invention and used in the methods of the invention comprises in an aqueous solution 10 mM HEPES, 4% (w/v) Bovine serum albumin, 120 mM sodium perchlorate, optionally 1 mM Calcium chloride and optionally 0.05% (v/v) Proclin® 300. The pH is adjusted to 7.5 using sodium hydroxide. It is understood that a plurality of different, e.g. commercially available incubation reagents comprising similar amounts of BSA and a chaotropic salt like sodium perchlorate are equally suited to be comprised in the kits of the invention and can be used in the methods of the invention. Likewise the above mentioned uses of the cell treatment composition of the present invention are not limited to this specific embodiment of the incubation reagent.

According to a preferred embodiment the washing composition comprised in the kits of the invention and used in the methods of the invention comprises in an aqueous phosphate buffered saline (potassium free) solution 0.5% (w/v) of a 37% Formaldehyde solution, optionally 0.1% (v/v) a non-ionic surfactant, such as PLURONIC F68 (Life Technologies, Carlsbad, Calif.) and optionally 0.05% (w/v) Sodium lauroyl sarcosinate. It is understood that a plurality of different, e.g. commercially available washing compositions comprising similar amounts of formaldehyde and detergents are equally suited to be comprised in the kits of the invention and can be used in the methods of the invention. Likewise the above mentioned uses of the cell treatment composition of the present invention are not limited to this specific embodiment of the washing composition. It is understood that the present application may contain one or more further aspects and/or embodiments. Such aspects and/or embodiments may cover one or more of the above described features in isolation or in any combination with each other.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

DESCRIPTION OF FIGURES

FIG. 1: Flow cytometric analysis of CD14-FITC and Stat5-PE staining of whole blood and the effect of GM-CSF activation of the blood FIG. 1 shows four flow cytometric scatter plots obtained by treating a whole blood sample with a method according to the invention (see example 2) and subsequent analysis on a FC500 cytometer (Beckman Coulter, Brea, Calif.). Scatter Plot A is showing the analysis of non-activated whole blood. Scatter Plot B is showing a 525 nm fluorescence analysis of CD14-FITC stained monocytes. In scatter plot C, p-Stat5-PE staining of the non-activated blood is shown. In scatter plot D, the whole blood sample was activated by GM-CSF prior to fixation. As compared to scatter plot C it can be seen in scatter plot D that monocytes and neutrophils express p-Stat5 after GM-CSF activation. I=granulocytes; II=Lymphocytes; III=CD 14$^+$ Monocytes; IV=p-Stat-5$^+$ Monocytes.

EXAMPLES

Example 1

Exemplary Preparation of Compositions According to the Invention

The following compositions provide examples of suitable reagents within the scope of the present invention.

The fixation reagent (Reagent A) for the fixation of a biological sample comprising white blood cells, preferably a whole blood sample, comprises in an aqueous solution:

| Sodium Chloride | 150 mM |
| Formaldehyde (methanol-free) | 10% (w/v) |

Reagent A is of neutral pH and was filtered through nylon filter of 0.22 μm pores size.

The cell treatment composition (Reagent B) for the treatment of a biological sample comprising white blood cells, preferably a whole blood sample, comprises in an aqueous solution:

| Sodium dodecyl sulphate | 34.7 mM |
| Bovine serum albumine (BSA) | 1% (w/v) |
| Sodium dihydrogen phosphate | 2 mM |
| Sodium perchlorate | 150 mM |
| Proclin ® 300 | 0.05% (v/v) |

Reagent B was prepared by dissolving the sodium dodecyl sulfate in water. All ingredients with the exception of sodium perchlorate were mixed and the pH was adjusted to 4.4. Then sodium perchlorate was added and any occurring precipitation was dissolved by thorough mixing. The final pH is adjusted to 4.2 by the addition of NaOH. The composition was filtered through nylon filter of 0.22 μm pores size. Proclin® 300 was obtained from Supelco, SIGMA Aldrich (St. Louis, Mo., USA).

The incubation reagent (Reagent C) for the incubation of fixed and permeabilized cells comprises in an aqueous solution:

| HEPES | 10 mM |
| Bovine serum albumin | 4% (w/v) |
| Sodium Perchlorate | 120 mM |
| Calcium chloride | 1 mM |
| Proclin ® 300 | 0.05% (v/v) |

The pH is adjusted to 7.5 using sodium hydroxide. Reagent C was filtered through nylon filter of 0.22 μm pores size. Proclin® 300 was obtained from Supelco, SIGMA Aldrich (St. Louis, Mo., USA)

The washing composition (Reagent D) for the washing and conservation of cells after the incubation in reagent C comprises in an aqueous solution.

| Phosphate buffered saline (potassium free) | |
| Formaldehyde solution (37%) | 0.5% (w/v) |
| Non-iconic surfactant (PLURONIC F68) | 0.1% (v/v) |
| Sodium lauroyl sarcosinate | 0.05% (w/v) |

Reagent D was filtered through nylon filter of 0.22 μm pores size.

Example 2

Labeling of Cell Surface Antigens

To a volume of 100 μl of whole blood treated with 0.7 mM ethylenediamine tetraacetic acid (EDTA) as anticoagulant, 65 μl of fixation reagent (Reagent A of Example 1) was added. The mixture was vortexed and then incubated for 10 minutes at room temperature (18-25° C.). After 10 minutes, 1 ml of cell treatment composition (Reagent B of Example 1) was added. The mixture was vortexed shortly and allowed to incubate for 5 minutes at 37° C.

The pH of the anti-coagulated blood was approximately 7.2. After 10 minutes of fixation, the blood had a pH of approximately 6.1 due to the destruction of amino-groups. After addition of the cell treatment composition and 5 minutes of incubation the mixture had a pH of approximately 5.6.

The obtained mixture was then centrifuged at approximately 300 g and the liquid phase was removed. The pellet was taken up in 100 μl of incubation reagent (Reagent C of Example 1) and dissolved by vortexing. The pH of the obtained mixture was approximately 7.0.

To the incubation mixture the following conjugated monoclonal antibody products were added in a volume as indicated by the manufacturer as one test.

IgG1 FITC isotypic control (IM0639U, Beckman Coulter, Brea, Calif.)
IgG1 PE isotypic control (IM0670U, Beckman Coulter, Brea, Calif.)
CD14 FITC (IM 0645U, Beckman Coulter, Brea, Calif.)
CD14 APC (IM 2580U, Beckman Coulter, Brea, Calif.)
CD45 FITC (IM0782U, Beckman Coulter, Brea, Calif.)
CD45 KO (A96416, Beckman Coulter, Brea, Calif.)
CD3 FITC (IM1281U, Beckman Coulter, Brea, Calif.)
CD19 PE (1M1285U, Beckman Coulter, Brea, Calif.)
CD34 PE (1M1871U, Beckman Coulter, Brea, Calif.)

After 15 minutes of incubation at room temperature, the sample was washed, taken up in a washing composition (reagent D of Example 1) and analyzed on a FC500 cytometer (Beckman Coulter, Brea, Calif.). The results of this experimental analysis are given in FIG. 1. From this data it is apparent that the methods according to the invention did on the one hand not impede the labeling of the cell surface marker CD14 and on the other hand provided access to the intracellular p-Stat5 epitope of monocytes and neutrophils (labeled generally as granulocytes in Table 1) that were activated with GM-CSF prior to the cell treatment (see experiment 2B) according to the invention.

In table 1 the signal to noise ratios (S/N) of some representative cell surface antigens are provided for lymphocytes, monocytes and granulocytes that were subjected to the cell preparation treatment according to the embodiment of the invention as given in example 2. The S/N ratios are calculated by the division of the mean fluorescence value of the labeled subpopulation and the same subpopulation treated with the isotypic control antibodies. In the case of the CD34 antigen, cells of the KG1 cell line (ATCC, Manassas, Va.) were spiked into the blood sample before treatment. The data indicates that all of the employed cell surface markers (CD3, CD14, CD19, CD34, CD45) were easily accessible by corresponding antibodies, thus demonstrating that cell surface antigens are conserved and retained accessible in the course of the cell treatment methods according to this invention.

TABLE 1

| Antibodies | Signal/Noise Lymphocytes | Signal/Noise monocytes | Signal/Noise granulocytes |
| --- | --- | --- | --- |
| CD14 FITC |  | 54.3 |  |
| CD45 FITC | 41.9 | 81.8 | 53.9 |
| CD3 FITC | 25.0 |  |  |
| CD19 PE | 20.0 |  |  |
| CD34 PE |  |  | 25.0 (KG1 Cell line) |

Labeling of Phosphorylated Intracellular Antigens

Aliquots of whole blood (anticoagulated with 0.7 mM EDTA) were incubated at 37° C. for 15 minutes in the presence of one of the following activating agents;
  GM-SCF (rhGM-CSF, 10 ng/ml—R&D Systems, Minneapolis, Minn.)
  IL2 (rhIL2, 20 ng/ml—R&D Systems, Minneapolis, Minn.)
  PMA (Phorbol Myristate Acetate PHA-L, 2 µg/ml—Sigma Chemical Corp., St Louis, Mo.)
  LPS (Lipopolysaccharide, 2 ng/ml—Sigma Chemical Corp., St Louis, Mo.)
  Interferon alpha (Rh Interferon alpha, 20 ng/ml—PBL Biomedical Laboratories, Piscataway, N.J.)
  IL6 (rhIL6, 200 ng/ml—R&D Systems Minneapolis Minn.)

The activated blood was then processed according to Example 2 To the incubation mixture the following conjugated monoclonal antibody products were added in a volume as indicated by the manufacturer as one test.
  Mouse anti-Stat5 (pY694)-PE (BD Biosciences Pharmingen, San Jose, Calif.)
  Mouse Phospho-p44/42 MAPK (Erk1/2) (Thr202/Tyr204) (E10) Alexa Fluor® 647 (Cell Signaling Technology Inc., Danvers, Mass.)
  Phospho-p38 MAPK (T180/Y182) Alexa Fluor® 488. (Cell Signaling Technology Inc., Danvers Mass.)
  Phospho-Stat1 (Tyr701) (58D6) Alexa Fluor® 488. (Cell Signaling Technology Inc., Danvers, Mass.)
  Phospho-Stat3 (Tyr705) (3E2) Alexa Fluor® 488. (Cell Signaling Technology Inc., Danvers, Mass.)
  Phospho-Stat5 RPE (B23139, Beckman Coulter, Brea, Calif.)

After 15 minutes of incubation of the samples at room temperature, the samples were washed and taken up in washing reagent and analyzed on a FC500 cytometer (Beckman Coulter Brea, Calif.). The obtained experimental data is provided in scatter plot C and D of FIG. 1. This data indicates, that intracellular phosphorylated epitopes of fixed cells that were treated according to the method of the invention are readily accessible to corresponding antibodies.

In table 2 the signal/noise (S/N) ratio of white blood cell subpopulations labeled with different anti-phospho-epitope antibodies are shown. The S/N ratio was calculated by the division of the mean fluorescence value of the subpopulations in activated blood aliquots and the mean fluorescence value from the respective subpopulations in non-activated aliquots of the same blood.

TABLE 2

| Activating agent | Antibodies | Signal/Noise Activated/non-acivated Lymphocytes | Signal/Noise Activated/non-acivated Monocytes | Signal/Noise Activated/non-acivated Ganulocytes |
| --- | --- | --- | --- | --- |
| GM-CSF | P-Stat5-PE | 1.1 | 3.5 | 6.7 |
| IL2 | P-Stat5 | 3.6 | 0.88 | 1.0 |
| PMA | P-ERK1/2 | 6.9 | 5.6 | 2.2 |
| LPS | P-p38 | 1.5 | 3.0 | 2.8 |
| Interferon alpha | P-Stat1 | 6.8 | 9.8 | 4.0 |
| IL6 | P-Stat3 | 1.8 | 2.0 | 0.6 |

The labeling of the different phospho-proteins of the three major white blood cell populations: lymphocytes, monocytes and neutrophils (a subtype of granulocyte), was compared between the non-activated blood and the blood after activation with an appropriate activator.

Example 3

To evaluate the influence of the anionic surface active agent concentration, various cell treatment compositions were prepared as outlined in example 1, although with varying SDS concentrations. Table 3 contains related experimental data demonstrating the influence of the SDS concentration in the cell treatment composition on the unmasking of phospho-epitopes like e.g. p-Stat5. In this setting optimal unmasking and staining of p-Stat5 was obtained using a cell treatment solution having a concentration of 1% w/v (34.7 mM).

TABLE 3

| SDS concentration of cell treatment composition | Signal/noise anti-Stat5 (pY694)-PE of activated/non-activated monocytes |
| --- | --- |
| 0.4% | 1.74 |
| 0.6% | 2.43 |
| 0.8% | 2.44 |
| 1.0% | 3.01 |
| 1.5% | 1.97 |
| 2.0% | 1.52 |

Example 4

For the reason of comparison of different anionic surface active agents, two different cell treatment compositions according to the present invention were prepared, one with sodium dodecyl sulfate (SDS) and the other with sodium dodecylbenzene sulfonate (SDBS, Aldrich technical grade, Sigma Chemical Corp., St Louis, Mo.), wherein both reagents were contained in the cell treatment composition at 34.7 mM. The pH values of the SDS containing cell treatment composition were as indicated in example 1. For reasons of precipitation and stability, the pH of the SDBS containing cell treatment composition was 5.95 and increased to 6.6 after the addition of the whole blood sample. Otherwise, the samples were processed and analyzed as given in Examples 2A and 2B.

As shown in Table 4, both reagents gave similar expression values for p-Stat5. The protection of the cells however was less efficient in the SDBS comprising reagent. Probably this is due to the higher pH, effecting the cell protection.

TABLE 4

| Detergent | Staining of monocytes | |
|---|---|---|
| | Signal/noise CD14-APC | Signal/noise activated/ non-activated p-Stat5-RPE |
| Sodium dodecyl sulphate 34.7 mM | 25.9 | 22.0 |
| Sodium dodecyl-Benzene-sulfonate 34.7 mM | 5.3 | 20.1 |

Example 5

This experiment shall demonstrate the protective effect of serum albumin at an acidic pH with regard to cells and antigens. For this purpose several cell treatment compositions were prepared as outlined in example 1, however with the following modification:
1. The cell treatment composition of example 1 in which the BSA was omitted and replaced by 20 mM acid phosphate having a buffering capacity at this concentration similar to the cell treatment composition of example 1. The pH of this reagent was 2.5.
2. The cell treatment composition of example 1, having a pH 4.15.
3. The cell treatment composition of example 1. The pH of the reagent was adjusted to 5.6.
4. The cell treatment composition of example 1. The pH of the reagent was adjusted to 6.28.
5. The cell treatment composition of example 1. The pH of the reagent was adjusted to 7.4.

The samples were processed as outlined in example 2, with the exception that the samples were washed with PBS after the fixation.

After the addition of fixed blood cells, the pH of the mixture of fixed blood and the five different cell treatment compositions as given above adjusted to the following values respectively:
1. pH=5.7
2. pH=5.7
3. pH=6.4
4. pH=6.7
5. pH=7.0

The CD14 antigen is particularly sensitive to denaturizing conditions and has been chosen as a parameter of protection. Also the side scatter of the monocytes and the number of recovered cells are indicated as parameters. Whole blood was processed and analyzed as shown in Example 2A and 2B.

At pH 5.7 of the analyzed mixture the highest protective effect of the serum albumin was observed. As can been seen from the table 5, the acidic effect can be related to the serum albumin. Under acidic conditions in the absence of serum albumin there is no increased protection. The signal/noise ratio of CD14 was calculated as shown in example 2.

TABLE 5

| | lysis mixture | | | | | |
|---|---|---|---|---|---|---|
| parameter | pH 5.7 Without serum albumin | pH 5.7 With sample serum albumin | pH 5.7 With sample Serum albumin and added BSA | pH 6.4 With sample Serum albumin and added BSA | pH 6.7 With sample Serum albumin and added BSA | pH 7.0 With sample Serum albumin and added BSA |
| s/n CD14 Antigen on monocytes | 7.7 | 32.3 | 72.6 | 62.3 | 52.4 | 51.0 |
| Side scatter Value of monocytes | 127.8 | 110.5 | 124.1 | 97.5 | 98.3 | 100.1 |
| Total number of monocytes | 212 | 239 | 330 | 260 | 256 | 257 |
| Total number of leukocytes | 3496 | 4813 | 4635 | 4033 | 4101 | 4167 |

Serum albumin at acidic conditions also seems to provide an additional fixation effect. Side scatter values of monocytes after blood lysis at acidic conditions tend to be higher as compared with the monocyte side scatter values of monocytes after blood lysis at neutral conditions (see table 5). This higher side scatter is irrespective of the presence of serum albumin. Side scatter augments with the opaqueness of cells and the amount of macromolecular aggregation in the cells. As the amount of macromolecular aggregation is a measure of the intensity of fixation of the cells, one may therefore draw the conclusion that the use of serum albumin under acidic conditions provides a better fixation effect.

Example 6

To compare the protective effect of serum albumin as opposed to other water soluble proteins, an alternative cell treatment composition comprising bovine milk casein (Sigma) instead of BSA was prepared. The other ingredients of this cell treatment composition were identical to the Reagent B of Example 1.

Whole blood was processed and analyzed as provided in Example 2A.

As can be seem from table 6, Serum albumin is superior to casein with regard to the protection of the cell surface antigen CD14. The signal/noise ratio of CD14 was calculated as shown in example 2. Both the side scatter values for monocytes and overall leukocytes are provided as a function of the fixation of cellular proteins by BSA or casein. Again the results indicate that BSA is more effective here than casein. Also the numbers of obtained monocyte and overall leukocytes was significantly reduced when using casein in the cell treatment composition instead of BSA, indicating that the protective effect of serum albumin is superior to casein.

TABLE 6

| Parameter | Lysis mixture | |
|---|---|---|
| | With serum albumin and added BSA | With serum albumin and added casein |
| s/n CD14 antigen on monocytes | 25.9 | 12.0 |
| side scatter value of monocytes | 116 | 93.6 |
| total number of monocytes | 1628 | 712 |
| side scatter value of leukocytes | 639 | 402 |
| total number of leukocytes | 21871 | 15605 |

Example 7

In some embodiments of the invention chaotropic salts like persulfate or thiocyanate may be comprised by the cell treatment composition. To illustrate the effect of e.g. sodium persulfate, the following cell treatment compositions were prepared:
  (1) The cell treatment composition of example 1 in which the sodium persulfate was omitted and replaced by 150 mM sodium chloride.
  (2) The cell treatment composition of example 1 in which the sodium persulfate was omitted and replaced by 150 mM sodium chloride. The SDS concentration in this reagent was modified into 1.5% instead of 1%.
  (3) The cell treatment composition of example 1.

Whole blood was processed and analyzed as shown in example 2A and B. The signal to noise ratios (s/n) were calculated as shown in example 2A and B.

Exchanging sodium persulfate for sodium chloride in the cell treatment composition (1) resulted in incomplete lysis of the red blood cells. This effect could be compensated by increasing the SDS concentration of the cell treatment composition to 1.5% SDS (solution (2)), which could produce a comparable lysis effect as it was obtained with (1). Also the expression of p-Stat5 was comparable. However, the advantage of using the chaotropic salt persulfate instead of a higher concentration of SDS became apparent by the better protection of the CD14 antigen (see Table 4).

TABLE 7

| parameter | lysis mixture | | |
|---|---|---|---|
| | Lysis reagent; 0.15 mM sodium perchlorate 1%(w/v) SDS | Lysis reagent; 0.15 mM sodium chloride 1%(w/v) SDS | Lysis reagent; 0.15 mM sodium chloride 1.5%(w/v) SDS |
| Lysis time | 2 minutes | Incomplete lysis | 2 minutes |
| s/n of p-Stat5-PE | 3.43 | — | 2.38 |
| s/n of CD14-FITC | 41.1 | — | 9.0 |

Example 8

The following displays exemplary solutions which may be used in the system and method according to the present invention.

For example, a composition for the fixation of whole blood according to the present invention may be an aqueous solution of Sodium Chloride (150 mM) and Formaldehyde methanol-free (10% (w/v)) at neutral pH. The composition is filtered through nylon filter of 0.22 μm pores size.

Further, a composition for the lysis and the denaturation of fixed whole blood according to the present invention may be an aqueous solution of Sodium dodecyl sulphate (34.7 mM), Methanol (1% v/v), Bovine serum albumine (1% w/v), Sodium dihydrogen phosphate (2 mM), and Sodium perchlorate (150 mM). The pH is adjusted to 4.2 using hydrochloric acid.

The composition for the lysis and the denaturation of fixed whole blood according to the present invention is prepared by mixing the components except for the sodium perchlorate. The volume should be 85% of the final volume. Then the pH is adjusted at 4.4. A solution of 1M sodium perchlorate is added to the final volume.

After that the composition is mixed thoroughly to dissolve precipitation in order to obtain a final pH of 4.2. Finally, the composition was filtered through nylon filter of 0.22 μm pores size.

Further, a composition for the incubation of lysed and permeated cells according to the present invention with antibody may be an aqueous solution of 4-(2-Hydroxyethyl) piperazine-1-ethanesulfonic acid (HEPES) (10 mM), Bovine serum albumin (2% (w/v)), Sodium Chloride (150 mM), and Proclin® 300 (0.05%). After mixing the pH is adjusted to 7.5 using sodium hydroxide. Finally, the composition is filtered through nylon filter of 0.22 nm pores size. Proclin® 300 was obtained from Supelco, Sigma Chemical Corp., St Louis, Mo., USA).

A composition for the washing and conservation of the antibody stained cells according to the present invention may an aqueous solution of Phosphate buffered saline (potassium-free), and Formaldehyde methanol-free (0.5% (w/v)).

What is claimed is:
1. A kit comprising:
  a cell treatment composition comprising:
    (a) at least one anionic surface active agent which is comprised in said composition in a concentration of between 0.3% and 2% (w/v), wherein a salt of said anionic surface active agent is represented by the formula (1):

$$Y-SO_3^-X^+ \qquad (1)$$

wherein Y is either R—O or R, and R represents an alkyl, alkylene, aryl, alkylene-alkyl, aryl-alkyl or aryl-alkylene group having 8 to 18 carbon atoms and X represents a monovalent cation, and
    (b) serum albumin which is comprised in said composition in a concentration of between 0.2% and 20% (w/v),
    wherein the pH of said cell treatment composition is in a range equal or greater than 2 and equal or less than 6 and wherein the at least one anionic surface active agent is sodium dodecyl sulfate (SDS) or sodium dodecylbenzenesulfonate (SDBS); and
  a cell incubation reagent comprising:
    serum albumin, perchlorate or thiocyanate, a preservative and a buffer having a pKa in the neutral pH range, wherein the concentration of buffer is 1 to 50 mM and wherein the concentration of serum albumin is 0.2 to 20% (w/v) and wherein the perchlorate or thiocyanate concentration is 50 to 250 mM; and wherein the preservative concentration is 0.01 to 0.2% (v/v);

and having a pH from 6 to 9.

2. The kit according to claim 1, further comprising a washing composition having a pH from 7 to 7.5, said washing composition comprising:

phosphate buffered saline;

formaldehyde, the concentration of formaldehyde from 0.1 to 2% (v/v);

poloxamer 188, the concentration of poloxamer 188 from 0.01 to 1% (v/v); and lauroyl sarcosinate, the concentration of lauroyl sarcosinate from 0.005 to 0.05% (v/v).

3. The kit according to claim 1, further comprising at least one detectably labeled binding agent specific for an intracellular epitope.

4. The kit according to claim 1, further comprising at least one detectably labeled agent specific for an extracellular epitope.

5. The kit according to claim 1, further comprising a fixative reagent comprising formaldehyde.

6. The kit according to claim 1, wherein said anionic surface active agent is comprised in said cell treatment composition in a concentration of between 0.6% and 1.5% (w/v).

7. The kit according to claim 1, wherein said serum albumin is mammalian serum albumin.

8. The kit according to claim 1, wherein said serum albumin is bovine serum albumin.

9. The kit according to claim 1, wherein the pH of the cell treatment composition is between 3 and 5.5.

10. The kit according to claim 1, wherein the cell treatment composition further comprising a chaotropic salt.

11. The kit according to claim 10, wherein the chaotropic salt comprises a concentration of from 20 to 250 mM.

12. The kit according to claim 10, said chaotropic salt comprises perchlorate, thiocyanate, or a combination thereof.

13. A combination comprising the kit according to claim 1 and a biological sample.

14. The combination according to claim 13, wherein said biological sample comprises fixed white blood cells, whole blood, bone marrow, or an isolated subpopulation of leukocytes.

15. The combination according to claim 13, wherein said white blood cells comprising lymphocytes or monocytes.

16. A method of using the kit of claim 1, the method comprising the steps of:

treating a biological sample with the cell treatment composition of the kit of claim 1; and treating said biological sample with the cell incubation reagent of the kit of claim 1.

17. The method according to claim 16, further comprising the step of contacting said biological sample with a fixative, wherein said fixative is added in a sufficient amount to achieve at least partial cross-linking of proteins, lipoproteins and nucleic acid molecules.

18. The method according to claim 17, said method further comprising incubating said biological sample with said fixative for 5 to 15 minutes at a temperature of between 15° C. and 30° C.

19. The method according to claim 16, said biological sample comprising whole blood, bone marrow, or an isolated subpopulation of leukocytes.

20. The method according to claim 19, wherein said cell treatment composition permeabilizes at least white blood cells and unmasks intracellular epitopes of said white blood cells.

21. The method according to claim 20, wherein said intracellular epitopes comprise phospho-epitopes.

22. The method according to claim 20, said white blood cells comprising lymphocytes or monocytes.

* * * * *